US012073695B1

(12) United States Patent
Tulloch (10) Patent No.: US 12,073,695 B1
(45) Date of Patent: Aug. 27, 2024

(54) SELF-SANITIZING PAYMENT ASSEMBLY FOR DRIVE-THROUGH WINDOWS

(71) Applicant: Stephen Tulloch, Fort Lauderdale, FL (US)

(72) Inventor: Stephen Tulloch, Fort Lauderdale, FL (US)

( * ) Notice: Subject to any disclaimer, the term of this patent is extended or adjusted under 35 U.S.C. 154(b) by 464 days.

(21) Appl. No.: 17/544,040

(22) Filed: Dec. 7, 2021

Related U.S. Application Data

(60) Provisional application No. 63/161,489, filed on Mar. 16, 2021.

(51) Int. Cl.
   | | |
   |---|---|
   | *G07F 7/00* | (2006.01) |
   | *A61L 2/18* | (2006.01) |
   | *A61L 2/24* | (2006.01) |
   | *G06F 3/041* | (2006.01) |

(52) U.S. Cl.
CPC ............... *G07F 7/005* (2013.01); *A61L 2/18* (2013.01); *A61L 2/24* (2013.01); *A61L 2202/14* (2013.01); *G06F 3/041* (2013.01)

(58) Field of Classification Search
CPC ... G06K 13/06; H01R 12/89; H01R 13/62911
See application file for complete search history.

(56) References Cited

U.S. PATENT DOCUMENTS

| | | | |
|---|---|---|---|
| 2021/0289958 A1* | 9/2021 | Holmes | A47F 9/04 |
| 2021/0322600 A1* | 10/2021 | Altman | B08B 7/0057 |
| 2021/0330832 A1* | 10/2021 | Dobbins | G07F 9/10 |

* cited by examiner

*Primary Examiner* — Jamara A Franklin
(74) *Attorney, Agent, or Firm* — Allen, Dyer, Doppelt & Gilchrist, P.A.

(57) ABSTRACT

A self-sanitizing payment assembly comprising an enclosure assembly, a mounting assembly, a retractable lever assembly, a payment processor, a sanitizer and a plurality of sensors. The mounting assembly attaches the retractable lever assembly to a wall. The retractable lever assembly is disposable into and out of a plurality of expanded positions and a retracted position. The plurality of sensors may be configured with a processing unit to ascertain the position of the arm and/or hand of a user and automatically adjust the position of the payment processor and/or sanitizer to bring them closer to the user. The payment processor is configured to activate upon the sanitizer unit releasing or otherwise dispensing a sanitizer substance.

20 Claims, 8 Drawing Sheets

SELF-SANITIZING PAYMENT ASSEMBLY FOR DRIVE-THROUGH WINDOWS

FIELD OF INVENTION

The present invention relates to the field of self-sanitizing payment processing tools.

BACKGROUND

Existing drive-through systems are not equipped to address today's health challenges, including transmission of contagious illnesses such as COVID-19, SARS, MERS, influenza virus, etc. Drive through systems generally require direct contact between at least two individuals, including when a user provides payment to the staff person. Not only does this situation generally pose a risk of transmission between the staff and the users, but an added risk is involved when individuals exchange credit or debit cards, bills, coins, etc. Accordingly, there is a need in the industry to provide a self-sanitizing payment assembly that overcomes at least some of the aforementioned risks. A benefit would be provided by providing a self-sanitizing payment assembly with an enclosure assembly that could keep its other components concealed during periods of non-operation. An even further benefit would be provided if such a self-sanitizing payment assembly would comprise a retractable lever assembly comprising motorized components that could enable a pivotal movement between adjacently disposed segments. The industry would further benefit by providing a self-sanitizing payment assembly with a plurality of sensors configured to ascertain the position of the arm and/or hand of a user and automatically adjust its own position accordingly. An even further benefit would be provided by providing a self-sanitizing payment assembly with a sanitizer unit configured to dispense a sanitizer substance when the hand of a user is in sufficient proximity thereto.

SUMMARY

The present invention is directed to a self-sanitizing payment assembly intended to be used in connection with drive-through windows. The self-sanitizing payment assembly according to the present invention comprises an enclosure assembly, a mounting assembly, a retractable lever assembly, a payment processor, a sanitizer and a plurality of sensors. The payment processor may comprise a display, keypad, a credit card swipe processor, and/or other related components. The enclosure assembly may comprises at least two panels that may independently move in a lateral or direction, towards and/or away from one another. The panels may be collectively disposable into an out of a closed position, for periods of non-operation, and a plurality of open positions, for periods of operation.

The mounting assembly is generally disposed on an inside of the enclosure assembly and is intended to interconnect the retractable lever assembly to a wall surface with a brace. Brackets may be used to tie the brace to the wall surface via a variety of connecting mechanisms, e.g., screws, bolts, tapcons, epoxy, nails, etc. The self-sanitizing payment assembly comprises a retractable lever assembly, which is intended to interconnect the payment processor and sanitizer unit to the mounting assembly. The retractable level assembly may comprise a sleeve. The sleeve may be disposed in surrounding and slidable relation to the brace, and further may be movable up and/or down along the length of the brace, for example, via a variety of motorized components. The retractable lever assembly may comprise a first, second and/or third segment. The first and or second segment may be adjacently disposed and movable with respect to one another and may be collectively disposable into a plurality of expanded positions and/or retracted positions.

The self-sanitizing payment assembly according to the present invention comprises a plurality of sensors. The sensors may be cooperatively configured with the processing board to ascertain a position of a vehicle and/or user relative to the payment processor and/or sanitizer unit. Furthermore, the sensors may also be cooperatively configured with processing board to adjust the position of the components of the retractable lever assembly and/or the payment processor relative to the position of the arm and/or hand of the user. As such, the payment processor may be automatically disposed in proximity to the arm and/or hand of the user to allow him/her to access and operate the payment processor. For example, one or more of the plurality of sensors may ascertain the vertical and/or horizontal position of the arm and/or hand of the user. Thus, this may trigger an automatic movement, upwards or downwards, or in the horizontal direction, of the components of the retractable lever assembly as well as the payment processor and/or sanitizer.

Additional features of the present invention comprise providing a sanitizer unit that is operatively configured to automatically release a sanitizer substance upon detection of the arm of a user in proximity thereto. The sanitizer unit may comprise electronic components operatively configured with the processing unit and/or sensor(s) to automatically activate upon detection of an arm and/or hand of the user in proximity to the sanitizer unit. Furthermore, the payment processor may be configured to only activate and/or allow access to the user only upon the sanitizer unit releasing the sanitizer substance.

DETAILED DESCRIPTION

Figure 1:
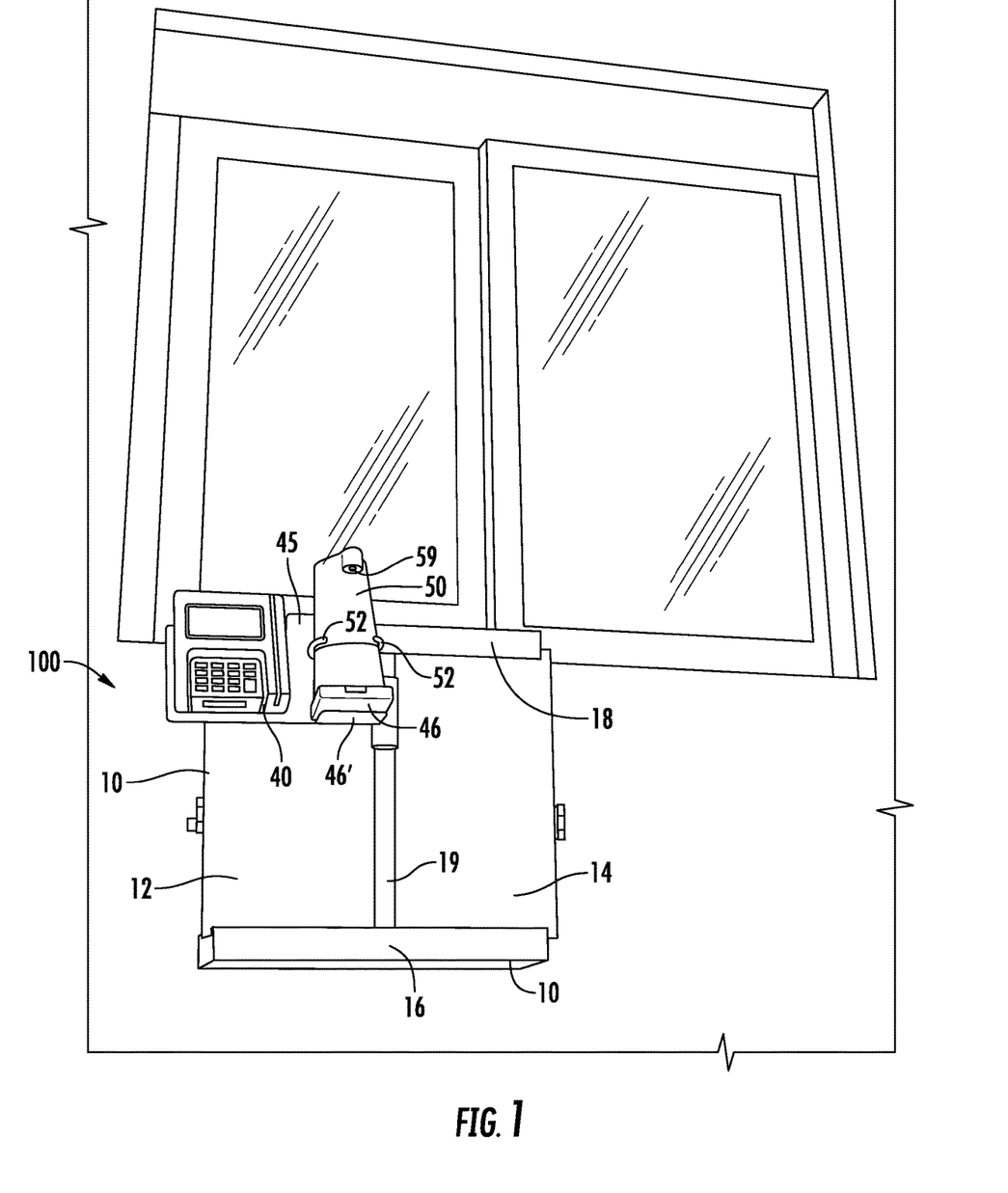
FIG. 1. is a front view of one embodiment of the self-sanitizing payment assembly according to the present invention installed on the wall of a drive-through window.

With initial reference to FIG. 1, the present invention is directed to a self-sanitizing payment assembly 1. The self-sanitizing payment assembly 1 according to the present invention is primarily intended to be used in connection with drive-through windows and related applications where a user needs to access a payment processor or payment processing unit from his/her vehicle. As shown throughout the Figures, a payment processor 40 may comprise a unit with a display, keypad, a credit card swipe processor, and/or other related components as may be required for a user to conduct a payment transaction. Such a payment transaction could be in connection with a variety of drive-through applications, including, but not limited to, food, beverage, groceries, laundry services, banking, etc. It is within the scope of the present invention that the innovative self-sanitizing payment assembly 1 also comprise an accessible sanitizer unit 50 or sanitizer unit.

Figure 2:
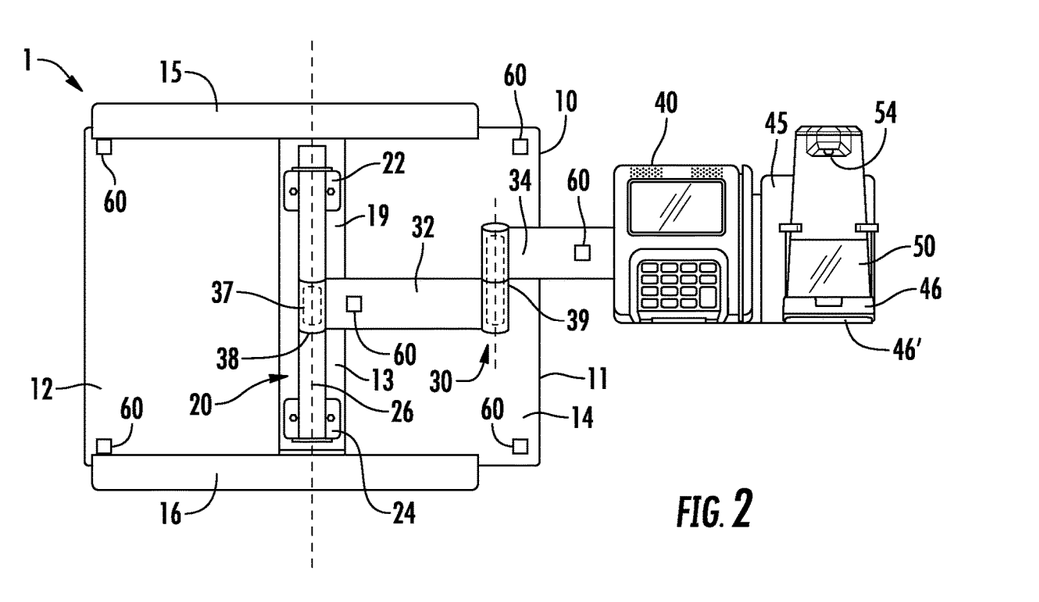
FIG. 2. is a front view of one embodiment of the self-sanitizing payment assembly according to the present invention comprising a retractable lever assembly disposed in an expanded position.
Figure 3:
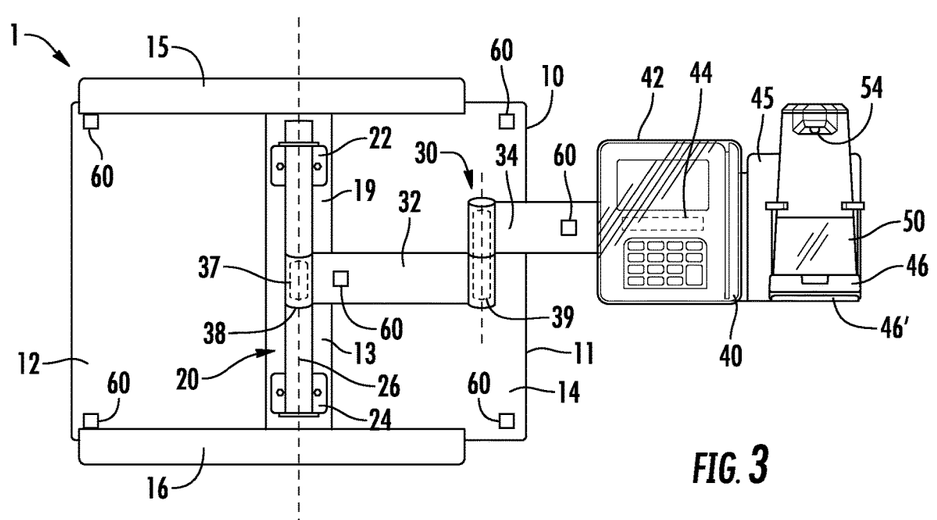
FIG. 3. is a front view of another embodiment of the self-sanitizing payment assembly according to the present invention comprising a retractable lever assembly disposed in an expanded position.
Figure 4:
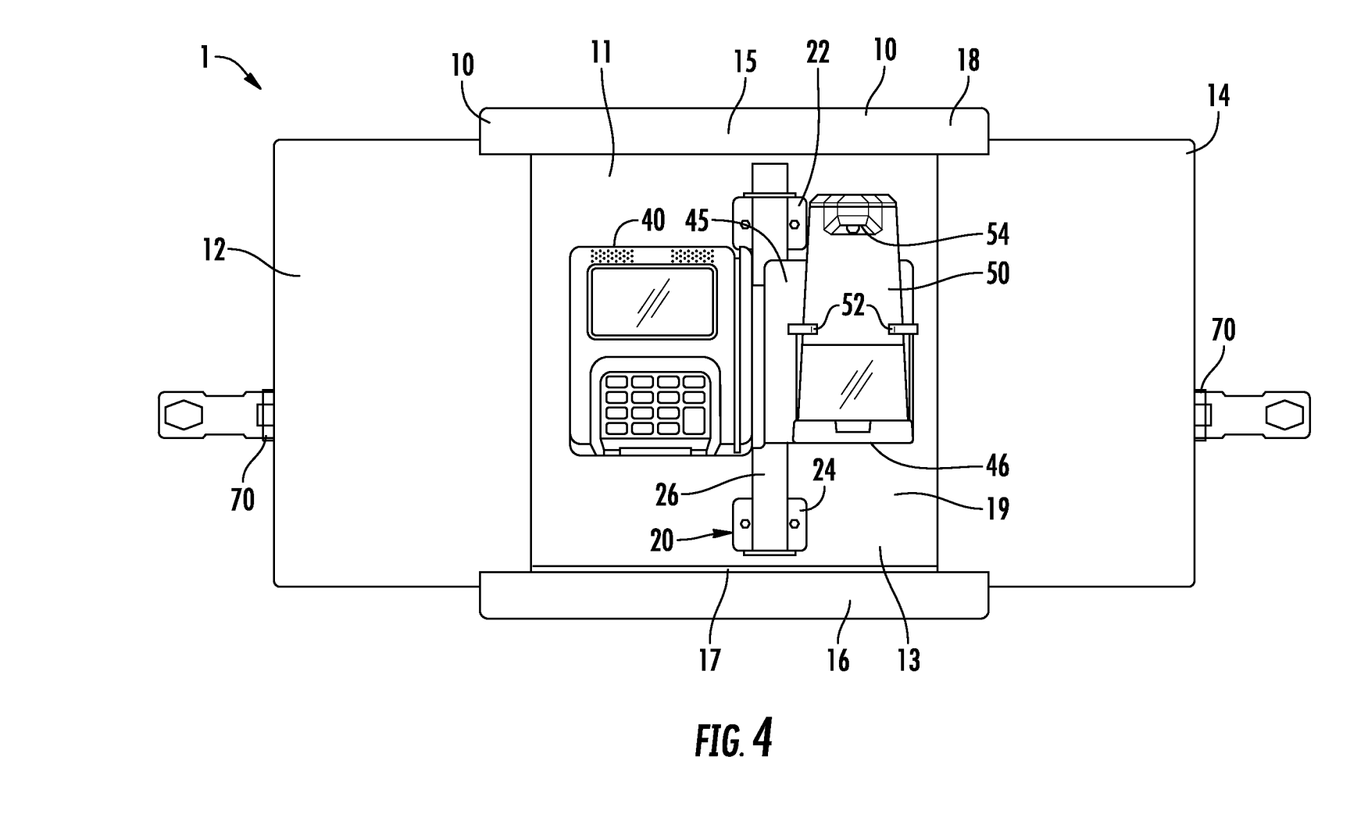
FIG. 4. is a front view of one embodiment of the self-sanitizing payment assembly according to the present invention comprising a retractable lever assembly disposed in a retracted position.
Figure 5:
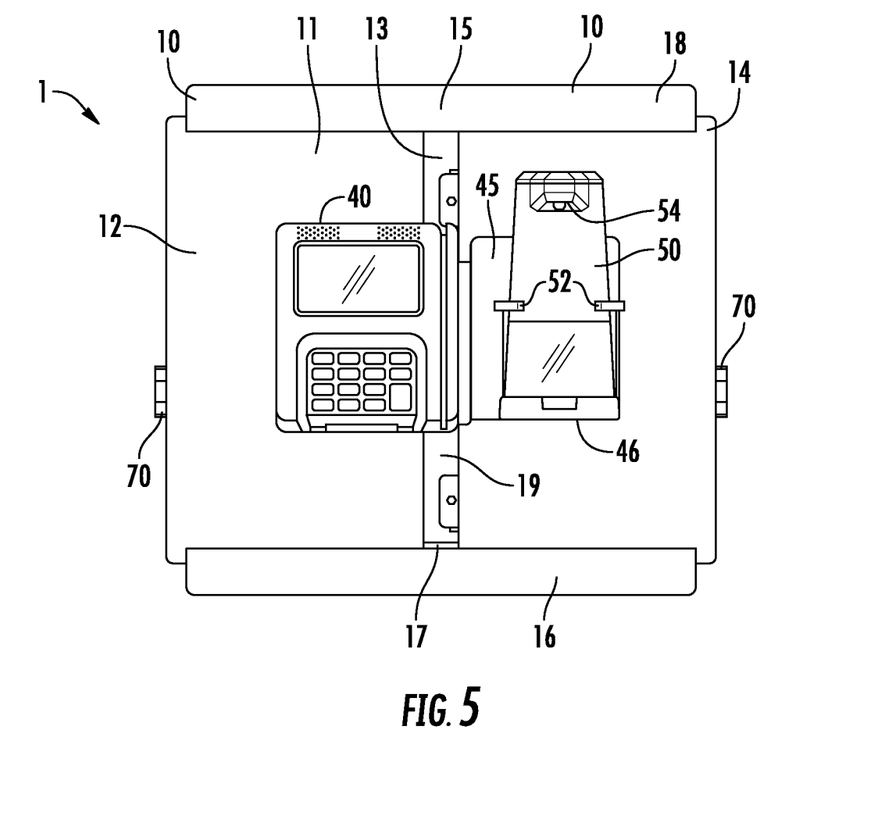
FIG. 5. is a front view of another embodiment of the self-sanitizing payment assembly according to the present invention comprising a retractable lever assembly disposed in a retracted position and comprising an enclosure assembly with the panels disposed in a semi-closed position.
Figure 6:
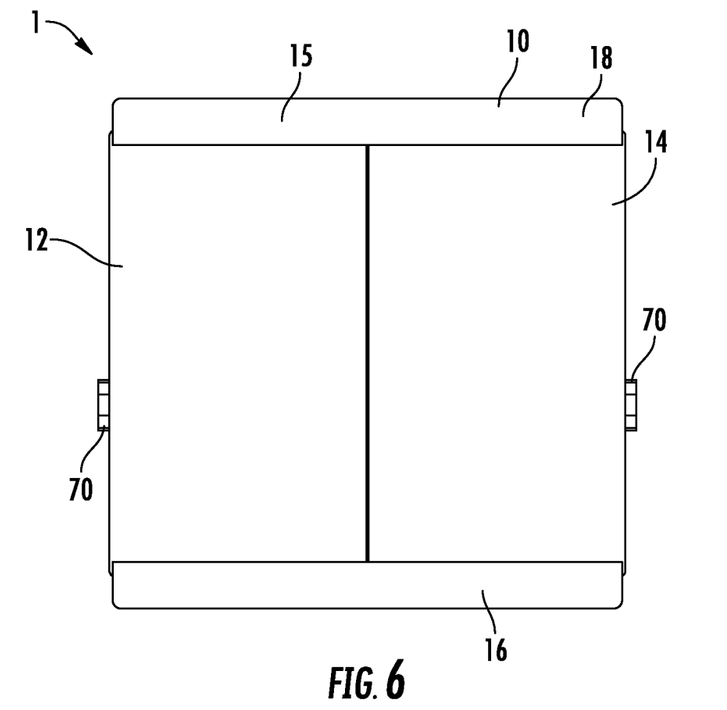
FIG. 6 is a front view of a further embodiment of the self-sanitizing payment assembly according to the present invention comprising an enclosure assembly with the panels of the enclosure assembly disposed in a closed position.

With reference now to FIGS. 1-7, the self-sanitizing payment assembly 1 comprises an enclosure assembly or wall enclosure assembly, indicated at 10. The enclosure assembly 10 primarily comprises a housing 11 and two panels 12 and 14. The panels 12 and 14 are laterally movable and may be collectively disposable into an out of a closed position, which is shown in FIG. 6. In the closed position, which is primarily intended for periods of non-operation, the panels 12 and 14 are intended to collectively define a cover over the open face 13 of the housing 11, which may protect the rest of the components of the self-sanitizing payment assembly 1, including the mounting assembly 20, the retractable lever assembly 30, the payment processor 40 and/or the sanitizer unit 50. The panels 12 and 14 may also be collectively disposable into and out of a variety of non-closed positions, e.g., as shown in FIGS. 1-5, during periods of operation of the innovative self-sanitizing payment assembly 1. As may be appreciated from FIGS. 1-6, the innovative self-sanitizing payment assembly 1 generally comprises a bottom guide 16 and a top guide 18. The bottom guide 16 is generally disposed around a lower section 17 of the housing 11, whereas the top guide 18 is generally disposed around an upper section 15 of the housing 11. The bottom guide 16 and/or top guide 18 may comprise a channel and/or an outside cap configured and dimensioned for placement of the first panel 12 and the second panel 14 such that both are in a slidable relation to the enclosure assembly 10. That is, the guides 16 and/or 18 should restrict movement of the panels 12 and/or 14 towards the inside of the enclosure assembly or outwards. As such, the only movement of the panels 12 and/or 14 that is contemplated is towards a corresponding side of each respective panel 12 and/or 14 on a plane that is substantially coincident with the front face of the enclosure assembly 10, e.g., as shown in FIG. 6. For example, it is contemplated that the panels 12 and/or 14 may move from the position as represented in FIG. 6 to the positions represented in FIG. 5 and/or FIG. 6 or other intermediate positions. Further, the guides 14 and/or 16 may be configured so that the panels 12 and/or 14 can no longer slidable move after they reach a predetermined point along bottom guide 16 and/or top guide 18, for example, as shown in FIG. 4.

Figure 7:
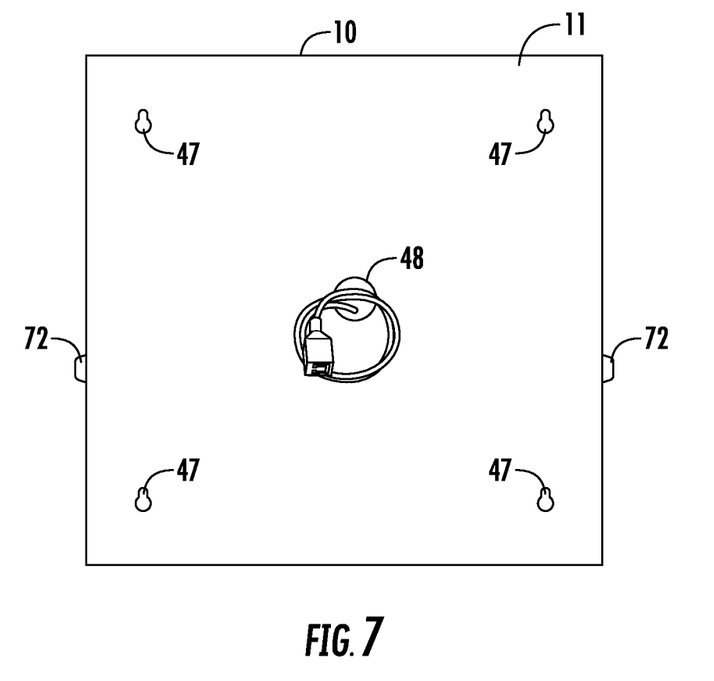
FIG. 7 is a rear view of one embodiment of a housing of the self-sanitizing payment assembly according to the present invention.

As is shown on FIG. 7, and as mentioned above, the enclosure assembly 10 may comprise a housing 11. The housing 11 may comprise a cubed or other related shape. Generally, the housing 11 also comprises an open face 13, which is generally oriented away from the wall surface or otherwise towards the area where users will be located when accessing the payment processing unit 40, whether the user is a pedestrian user or is inside of a vehicle. The housing 11 may comprise a variety of attachment mechanisms such that the enclosure assembly may be mounted on to a wall surface. For example, housing openings 47 may be provided around the corners of the back of the housing 11 and may be used as an attachment mechanism with a plurality of connectors, including, bolts, screws, tapcons, etc. In addition, as is also shown in FIG. 7, a central opening 48 may be provided for a variety of cable and/or other components, which may be operatively connected to the payment processing unit 40 and to another port, receptacle, or connection component. Furthermore, as shown in FIGS. 4-7, a locking mechanism may be provided to prevent the panels 12 and 14 from moving and maintaining the enclosure assembly in a closed position, i.e., as shown in FIG. 6. For example, a padlock or locking hasp staple 70, shown in FIGS. 4-6 unit may be provided with a rotating locking cylinder 72, shown in FIG. 7.

With reference to FIGS. 1-5, the self-sanitizing payment assembly 1 according to the present invention may be disposed into a plurality of open positions wherein the first panel 12 and the second panel 14 are disposed in a spaced apart relation to one another. In any one of the plurality of open positions, an aperture 19 may be substantially defined by the separation of the panels 12 and 14. The aperture 19 should comprise a sufficient size for the segments 32, 34, and/or 36 to pass there through, i.e., as shown in FIGS. 1 and 5. That is the size of the aperture 19 may initially be configured so that at least the retaining structure 45 may pass there through. But the size of the aperture 19 may be selectively reduced once the retaining structure 45 is outside of the housing 11, for example by placing the panels 12 and 14 closer to one another in order to minimize how much of the interior of the housing 11 is viewable from the outside.

As is perhaps best represented in FIG. 4, the self-sanitizing payment assembly 1 comprises a mounting assembly 20. The mounting assembly 20 is generally disposed on an inside of the wall enclosure assembly 10, including on an inside of the housing 11, but may be selectively positioned on an outside thereof, including on an outside of the housing 11. The mounting assembly 20 is intended to interconnect the retractable lever assembly 30 to the housing 11 and/or or the wall surface beneath it. More specifically, a brace 26 of the mounting assembly 20 may be connected to the housing 11 and/or the wall surface beneath it. Brackets 22 and/or 24 may be disposed substantially around the ends of the brace 26 and may connect the brace 26 to the housing 11, and consequently, the wall surface. A connector, e.g., screws, bolts, tapcons, epoxy, nails, etc., may be used to attach the brackets 22 and/or 24 to the housing 11.

With reference to at least FIGS. 2-3, the self-sanitizing payment assembly 1 comprises a retractable lever assembly 30. The retractable lever assembly 30 is intended to interconnect the payment processor 40 and sanitizer unit 50 with the mounting assembly 20. The retractable level assembly 30 comprises a sleeve 38 which is disposed in surrounding and slidable relation to the brace 26. Both the sleeve 38 and the brace 26 may comprise a plurality of cross sectional shapes, including a substantially circular, substantially square, substantially rectangular, etc. Accordingly, the sleeve 38 may be configured and dimensioned to surround the brace 26 and such that the retractable lever assembly 30 may move up or down along the length of the brace 26. Alternatively, such movement upwards or downwards along the length of the brace 26 may be achieved manually via a pneumatic sleeve 38, which may allow a user to selectively and manually position it. This may be enabled, for example, via a variety of motorized components, e.g., 37 which enable such slidable movement of the sleeve 38 along the length of the brace 26. Alternatively, such movement may be achieved manually. In addition, the sleeve 38 may be configured such that it is able to maintain a vertical position along the length if the brace 26 in the vertical direction, including accounting for the weight of the components of the retractable lever assembly 30 as well as the weight of the retaining structure 45, the payment processing unit 40 and/sanitizer 50. It is also within the scope of the present invention that the first segment 32 of the retractable lever assembly 30 be movable with respect to the brace 36. The first segment 32 may be pivotally movable with respect to the length of the brace 26, i.e., the first segment may be movable from left to right about the brace 26.

Figure 8:
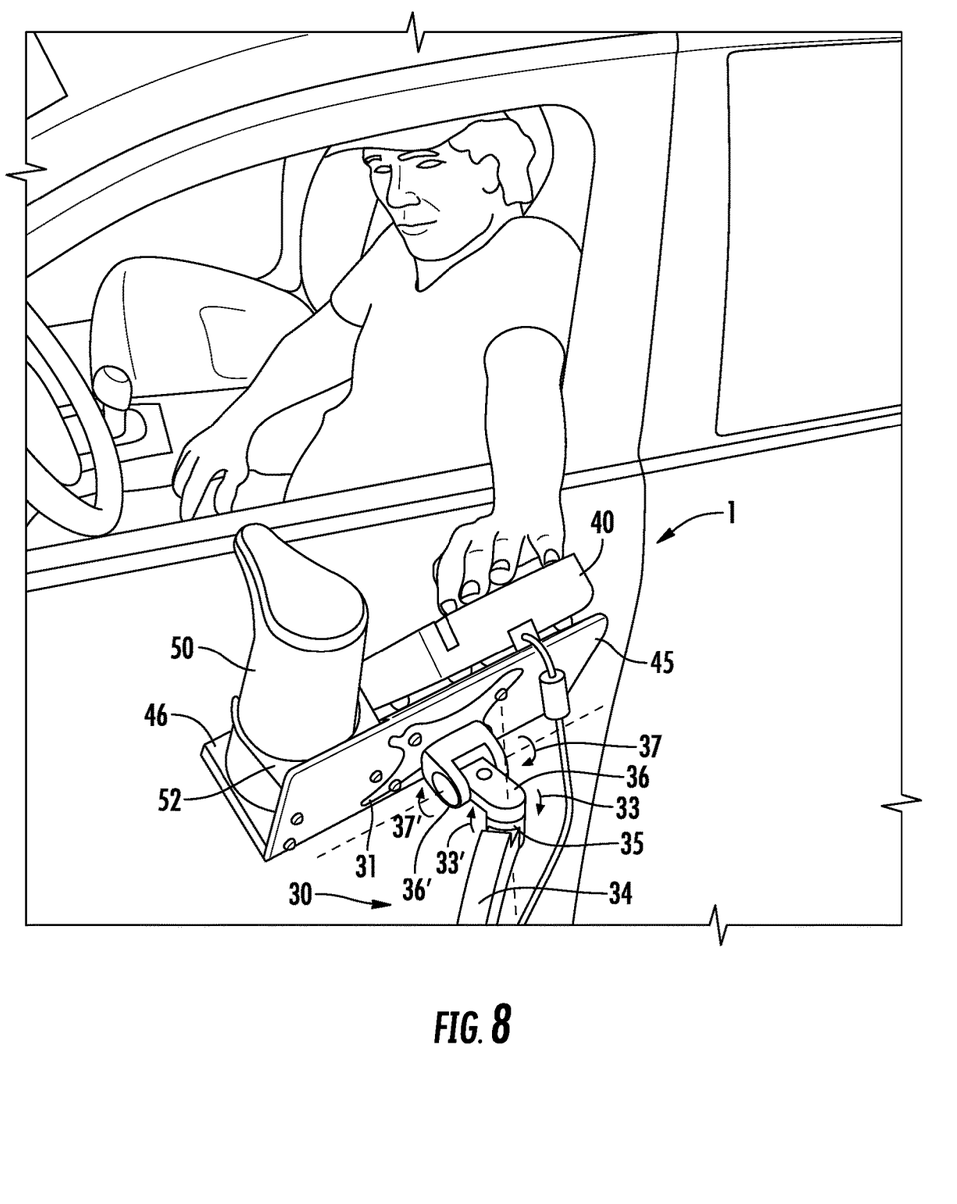
FIG. 8 is a rear view of one embodiment of a retaining structure of the self-sanitizing payment assembly according to the present invention.

Generally, the other components of the retractable lever assembly 30, i.e., segments 32, 34, and/or 36 may comprise pivotal connections, including, without limitation, hinged connections. Such pivotal connections are intended to at least partially enable a pivotal movement between the segments 32, 34, and/or 36 at their respective points of connection. Also the retaining structure 45 may comprise a hinged or otherwise pivotal connection to the second segment 34 and/or third segment 36. Also various motorized components may be provided at the foregoing connection points, i.e., between segments 32, 34 and/or 36, and between segments 34 and/or 32 and the retaining structure 45. For example, a the third segment 36 may be pivotally connected to the rear of the retaining structure 45, e.g., as shown in FIG. 8, such that it may be rotated upwards or downwards about a horizontal axis at the point of connection to the third segment 36. In the foregoing example, the horizontal axis may be substantially perpendicular to the length of the third segment. Moreover, pneumatic connections may be provided at these points of connection such that a relative alignment of the segments 32, 34, 36 with respect to one another and/or with respect to the retaining assembly 45, may be selectively enabled and/or maintained either by the use or automatically according to the position/location of the user and/or his/her hand(s) or arm(s).

As is perhaps best shown in FIG. 8, further features of the present invention are intended to allow a user to adjust a retaining structure 45 to physically access the payment processor 40. As shown in FIG. 8, a retaining structure 45 may be provided to securely retain the payment processor 40 and/or sanitizer 50. This may involve providing a bracket 31 attached to the retaining structure 45 and comprising a pivotal connection 36' to enable a pivotal movement between the retaining structure 45 and the third segment 36. As such, a user may adjust the position of the retaining structure 45 by rotating it along an axis defined along its length, i.e., along the directions represented at 37 and/or 37'. The retaining structure 45 may also be rotated along a vertical axis, i.e., along the directions represented at 33 and/or 33', given that the retractable lever assembly 30 may be provided with a third segment 36, which may be pivotally connected to the second segment 34. For example, a pivotal connection 35 or hinge-like connection 35 may be provided to interconnect segments 36 and 34. As is further shown at least is FIG. 8, a retainer 52 may be disposed on the retaining structure 45 and may be configured to hold the sanitizer 50 in place. A base 46 may be connected to the retaining structure 45 and may be configured to act as support to the sanitizer 50. As shown at least in FIG. 1, a base plate 46' may also be provided below the base 46 to provide additional support and/or to connect the base 46 to the retaining structure 45.

Also with reference to FIGS. 2-3, a second segment 34 of the retractable lever assembly 30 may be connected to and movable to the first segment 32. It is within the scope of the present invention that the first segment 32 and second segment 34 be movable with respect to one another. The first segment 32 and the second segment 34 may be pivotally movable with respect to one another. For example, motorized components 39 may be provided to enable such pivotal movement between the first segment 32 and the second segment 34. Additionally, other mechanical components may be provided so that the first segment 32 may be movable to the left and to the right of the second segment 34. Optionally, the third segment 36 may be interconnected to and movable with respect to the second segment 34. As such, a sanitizer unit 50 connected to a third segment 36 may move towards the second segment 34, and consequently towards the payment processor 40. It is within the scope of the present invention that the pivotal movement of the first segment 32 and the second segment 34, and/or of the second segment 34 and the third segment 36, should also allow the segments 32, 34 and/or 36 to move outward from the mounting assembly 20 and/or the enclosure assembly 10, such that the payment processor 40 and/or sanitizer unit 50 may be moved to a position that is closer to the vehicle of the user and/or the user.

With reference to at least FIGS. 1-4, the retractable lever assembly 30 may be disposed into and out of a plurality of expanded positions and retracted positions. For example, the segments 32, 34 and/or 36 of the retractable lever assembly 30 may be collectively disposed into an expanded position, shown at FIGS. 1-3, which are meant for periods of operation of the inventive self-sanitizing payment assembly 1. As a further example, the segments 32, 34 and/or 36 may be collectively disposed into a retracted position with respect to one another, for example, as shown in FIG. 4, such that all of the components of the retractable lever assembly 30 and/or the mounting assembly 20 may be stored on an inside of the enclosure assembly 10, as shown in FIG. 6. Said differently, in retracted positions, the segments 32, 34 and/or 36 of the retractable lever assembly 30 should be adjacently disposed to one another such that they may be enclosed within the panels 12 and/or 14 of the enclosure assembly 10. In one or more retracted positions the segments 32, 34 and/or 36 may also be disposed in an overlapping relation to one another. As such, the retractable lever assembly 30, the retaining structure 45, the payment processing unit 40 and/or the sanitizing unit 50 may be disposed in adjacent relation to one another to optimize space such that they may collectively fit on the inside of the housing 11.

With reference to at least FIGS. 2-3, features of the present invention comprise providing a self-sanitizing payment assembly 1 with a plurality of sensors 60. Each one of the plurality of sensors 60 may be operatively connected to a processing board or processing unit and may be configured to ascertain a position of a vehicle and/or user relative to the payment processor 40 and/or sanitizer unit 50. The sensors 60 may be proprietary or may be custom developed, and should configured to ascertain the position and/or movement of an object, i.e., a vehicle and/or arm of a user, in relative proximity. For example, the sensors 60 may comprise light sensors and/or motion sensors. The sensors 60 may gather data relating to the position and/or movement of an object.

The sensors 60 may convert this data into a signal that may be sent to a processor or otherwise processing board or unit such that it may be interpreted or otherwise processed. The processing board or unit may be operatively disposed with the motorized components 37 and/or 39 of the retractable lever assembly 30. As such processed or interpreted data relating to the position of a user may be associated with certain commands or instructions that may enable an automatic movement of the components of the retractable lever assembly 30 with respect to the position of the vehicle and/or user. The processor may be operatively connected to the plurality of sensors and/or various other components, i.e., segments 32, 34 and/or 36, panels 12 and/or 14, sleeve 38. As such the processor and the plurality of sensors 60 may be cooperatively configured to automatically adjust the position of the various components of the retractable lever assembly 30 and/or the retaining structure 45 according to the position of the user. By way of example, the sensors 60 may comprise light sensors configured to detect a positon of the hand or arm of a user. Further to this example, the processor and the plurality of sensors 60 may be cooperatively configured to automatically adjust the positon of the retaining structure relative to a detected position of the hand or arm of a user.

Also with reference to at least FIGS. 2-3, the present invention comprises providing positional adjustments based on the approximate location of the vehicle and/or user. For example, one or more of the plurality of sensors 60 may ascertain the vertical position of the arm and/or hand of the user, which may cause an automatic movement, upwards or downwards, of the sleeve 38, to a position that substantially matches the height of the arm and/or hand of the user with the approximate height of the payment processor 40 and/or sanitizer unit 50. As a further example, the plurality of sensors 60 may be configured to ascertain the horizontal position of the arm and/or hand of the user to cause an automatic horizontal movement of the first segment 32 and/or second segment 34, such that the horizontal position of the payment processor or processing unit 40 and/or sanitizer unit 50 substantially matches the horizontal position of the arm and/or hand of the user. As a further example, the sensors 60 may be configured to ascertain the depth separation between the payment processor 40 and the arm and/or hand of the user. In such example, the sensors 60 may be operatively configured with the processing unit and the retractable lever assembly 30 to automatically adjust the position of the payment processor away from the enclosure assembly 1 and/or underlying wall. In turn, this should result in bringing the payment processor 40 closer to the hand and/or arm of the user. By way of example only, one or more of the plurality of position sensors 60 may be manufactured by the company Arduino AG, including under the brand Arduino®. As an even further example, one or more of the plurality of sensors 60 may also incorporate laser optic capabilities, electro-optic capabilities, and other related technologies. Alternatively, it is also contemplated that the user may make manual adjustments to adjust the position, including angle of orientation, height, and or vertical position, of the retaining structure 45, and consequently the payment processor 40 and/or sanitizer 50.

Additional features of the present invention comprise providing a sanitizer unit 50 that is operatively configured to automatically release a sanitizer substance upon detection of the arm of a user. The sanitizer unit 50 may comprise a detection assembly 54 configured to automatically dispense a predetermined amount of the sanitizer substance upon detecting that an object, e.g., a user's hand or user's arm, is within sufficient proximity thereto. Optionally, the payment processor 40 may not be accessed or may not otherwise be turned on unless the sanitizer unit 50 releases a sanitizing substance. Said differently, the payment processor 40 may be configured to allow a user access only after the sanitizer unit releases a sanitizing substance, for example, onto the hand(s) of the user, and the user has a chance to disinfect his/her hands.

Even further features of the present invention comprise providing a retaining structure 45 that is movable with respect to the housing 41 and which may be disposed into and out of a plurality of operative orientations. For example, in at least one of the plurality of operative orientations, the first segment 12 and the second segment 14 are disposed in an open position, whereas the segments 32, 34, and/or 36 of the retractable lever assembly 30 are collectively disposed in at least one of the plurality of expanded positions. Additionally, in at least one of the plurality of operative orientations, the retaining structure may be disposed in sufficient proximity to and oriented towards the user. It is contemplated that in any one of the operative orientations, the user may be able to selectively adjust the position of the retaining structure 45, and consequently the payment processing unit 40 and/or sanitizing unit 50, according to his/her position, dimensional constraints, size of vehicle, etc.

As shown at least in FIG. 3, even additional features of the present invention comprise providing a payment processing unit 40 with a shield 42. The shield is primarily intended to at least partially prevent dirt or other infectious particles, including present in the hands and/or fingers of a user, from traveling or otherwise being transported to the payment processing unit 40 and/or its operable components, i.e., electronic touchscreen, keypad, manual keypad, etc. The shield 42 may comprise a material configured to permit an electric charge to pass there through, for example, a static charge from the finger of a user to operate an electronic touch screen of the payment processor 40. The shield 42 may also be provided with a flexible material configured to allow a user to access an underlying keypad, reducing the need for a direct contact with the key pad. The shield 43 may also comprise a flexible material configured and/or dimensioned to conform according to a pressure exerted by the finger(s) of the user to push down on the keys of a manual keypad. Additionally, the payment processor may be provided with an electronic card reader 44 configured to authenticate a component of the user. Such a component may comprise a credit or debit card, check book, driver's license, passport, or other related item capable of providing authentication. If an electronic card reader 44 is provided, the shield 42 may be provided with a material configured to allow an electronic signal to pass there through, for example to enable an operative communication between the electronic card reader 44 and the credit or debit card. In addition to, or in lieu of a card reader 44, the payment processor 40 may be provided with face recognition authentication capabilities, including components thereof, e.g., a built-in camera or an ancillary or separate camera.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A self-sanitizing payment assembly configured for attachment to a wall surface near a window, the self-sanitizing payment assembly comprising:
   an enclosure assembly comprising a housing, a first panel and a second panel, the first panel and the second panel collectively disposable into and out of a closed position and a plurality of open positions,
   a mounting assembly comprising a sleeve operatively connected to a brace, the brace disposed on an inside of the housing, the sleeve disposed in slidable and movable relation to the brace,
   a retractable lever assembly comprising a plurality of segments collectively disposable into and out of a retracted position and a plurality of expanded positions,
   a payment processing unit connected to a retaining structure, the retaining structure connected to at least one of the plurality of segments,
   a sanitizing unit connected to the retaining structure, and the retaining structure movable with respect to the housing and disposable into and out of a plurality of operative orientations.

2. The self-sanitizing payment assembly as recited in claim 1 wherein the housing comprises an open face along a front side thereof; the first panel and the second panel being disposed in a slidable, movable relation to the housing along the plane of the open face; the closed position comprising the first panel adjacently disposed to the second panel, and the first panel and the second panel collectively defining a cover around the open face the housing.

3. The self-sanitizing payment assembly as recited in claim 2 wherein the enclosure assembly further comprises a top guide disposed on an upper section of the housing and a bottom guide disposed on a lower section of the housing.

4. The self-sanitizing payment assembly as recited in claim 3 wherein each one of the top guide and bottom guide are disposed around the open face of the housing; the top guide and the bottom guide being cooperatively configured and dimensioned for insertion of the first panel and the second panel; the top guide structured to retain a top section of the first panel and the second panel; the bottom guide structured to retain a bottom section of the first panel.

5. The self-sanitizing payment assembly as recited in claim 3 wherein the first panel and the second panel are configured and dimensioned for lateral reciprocal movement along the length of the top guide and the bottom guide.

6. The self-sanitizing payment assembly as recited in claim 1 wherein in at least one of the plurality of open positions the first panel and the second panel are disposed in a spaced apart relation to one another collectively defining an aperture; the aperture comprising a sufficient size for the retaining structure to pass there through.

7. The self-sanitizing payment assembly as recited in claim 1 wherein the brace is disposed on a vertical orientation on an inside of the housing; the sleeve being configured to reciprocally move in a vertical direction along the length of the brace.

8. The self-sanitizing payment assembly as recited in claim 7 wherein the sleeve comprises a pneumatic sleeve configured to maintain a vertical position along the length of the brace.

9. The self-sanitizing payment assembly as recited in claim 7 wherein the retractable lever assembly comprises at least a first segment connected to the sleeve; the first segment configured to pivotally move about an axis defined along the length of the brace.

10. The self-sanitizing payment assembly as recited in claim 1 wherein the retractable lever assembly comprises a first segment and a second segment; the first segment connected to the sleeve and configured to move together with the sleeve along the height of the brace; the first segment and the second segment being pivotally connected and movable to one another.

11. The self-sanitizing payment assembly as recited in claim 10 wherein in the retracted position the first segment and the second segment are adjacently disposed and in overlapping relation to one another; in at least one of the plurality of expanded positions the first segment and the second segment are disposed in non-overlapping relation to one another.

12. The self-sanitizing payment assembly as recited in claim 10 further comprising a third segment pivotally connected to and movable to the second segment about a vertical axis at the point of connection between the second segment and the third segment; the retaining structure being pivotally connected to the third segment and being configured to rotate about a horizontal axis at the point of connection with the third segment.

13. The self-sanitizing payment assembly as recited in claim 12 further comprising a first motorized component structured to enable an automatic vertical movement of the sleeve with respect to the brace, a second motorized component structured to enable an automatic movement between the first segment and the sleeve, a third motorized component structured to enable an automatic movement between the second segment and the first segment, a fourth motorized component structured to enable an automatic movement between the second segment and the third segment, and a fifth motorized component structured to enable an automatic movement between the retaining structure and the third segment.

14. The self-sanitizing payment assembly as recited in claim 1 wherein at least one of the plurality of operative orientations comprises the first and second segment disposed in at least one of the plurality of open positions; the plurality of segments of the retractable lever assembly being disposed in at least one of the plurality of expanded positions and the retaining structure disposed in sufficient proximity to and oriented towards a user.

15. The self-sanitizing payment assembly as recited in claim 1 wherein the sanitizing unit comprises a detection assembly configured to ascertain a position of a hand of a user; the sanitizing unit being configured to dispense a sanitizing substance upon the detection assembly detecting that a the hand of a user is within sufficient proximity to the detection assembly.

16. The self-sanitizing payment assembly as recited in claim 15 wherein the payment processing unit becomes operable only after the sanitizing unit dispenses a sanitizing substance.

17. The self-sanitizing payment assembly as recited in claim 1 wherein the payment processing unit comprises an electronic touch screen; the payment processing unit further comprising a shield comprising a material configured to permit an electric charge front the finger of the user to pass there through and operate the electronic touch screen.

18. The self-sanitizing payment assembly as recited in claim 1 wherein the payment processing unit comprises a manual keypad; the payment processing unit further comprising a shield comprising a flexible material configured to allow a user to manually exert a pressure sufficient operate each key of the manual.

19. The self-sanitizing payment assembly as recited in claim 1 further comprising a processor and plurality of sensors disposed around the wall enclosure assembly or the retractable lever assembly; the processor operatively connected to the plurality of sensors and to the plurality of segments of the retractable lever assembly; the processor and the plurality of sensors cooperatively configured to automatically adjust the position of the retaining structure.

20. A self-sanitizing payment assembly configured for attachment to a wall surface below or on a side of a drive through window, the self-sanitizing payment assembly comprising:
- an enclosure assembly comprising a housing with an open face, a first panel and a second panel, the first panel and the second panel collectively disposable into and out of a closed position and a plurality of open positions, the closed position comprising the first panel and the second panel adjacently disposed to one another and collectively defining a cover along the open face of the housing,
- a mounting assembly comprising a sleeve operatively connected to a brace, the brace disposed in a vertical orientation on an inside of the housing, the sleeve disposed in slidable movable relation along the length of the brace and structured to maintain a vertical position,
- a retractable lever assembly comprising a first segment, a second segment and a third segment collectively disposable into and out of a retracted position and a plurality of expanded positions; the first segment pivotally connected and movable to the brace and to the second segment; the second segment pivotally connected to and movable to the third segment;
- a payment processing unit connected to a retaining structure, the retaining structure pivotally connected to and movable to the third segment,
- a sanitizing unit connected to the retaining structure,
- the retaining structure movable with respect to the housing and disposable into and out of a plurality of operative orientations, and
- the enclosure assembly and the retractable lever assembly collectively disposable into and out of a storage position comprising the plurality of segments being collectively disposed into the retracted position and the first panel and the second panel are collectively disposed into the closed position.

\* \* \* \* \*